United States Patent
Kubo

[11] Patent Number: 5,295,983
[45] Date of Patent: Mar. 22, 1994

[54] URINARY COLLECTOR FOR WOMEN
[75] Inventor: Yoshinori Kubo, Oume, Japan
[73] Assignee: Akcare Co., Ltd., Tokyo, Japan
[21] Appl. No.: 969,430
[22] Filed: Oct. 30, 1992
[30] Foreign Application Priority Data
Nov. 1, 1991 [JP] Japan .................. 3-313472
[51] Int. Cl.5 .......................... A61F 4/44; A61B 5/00; B65D 81/00; A47K 11/00
[52] U.S. Cl. ..................... 604/329; 128/761; 4/144.3
[58] Field of Search ............... 128/760, 761; 604/329-331; 4/144.1-144.3

[56] References Cited
U.S. PATENT DOCUMENTS

| | | | |
|---|---|---|---|
| 3,349,768 | 10/1967 | Keane | 604/329 X |
| 3,958,561 | 5/9176 | Bucalo | 604/330 X |
| 4,202,058 | 5/1980 | Anderson | 4/144.3 |
| 4,270,539 | 6/1981 | Michaud | 4/144.3 |
| 4,713,065 | 12/1987 | Koot | 604/329 |
| 4,747,166 | 5/1988 | Kuntz | 604/329 X |
| 4,857,064 | 8/1989 | Mendoza | 4/144.2 X |
| 4,889,532 | 12/1989 | Metz et al. | 604/330 |
| 5,049,144 | 9/1991 | Payton | 604/329 |

FOREIGN PATENT DOCUMENTS

| | | | |
|---|---|---|---|
| 0794640 | 9/1968 | Canada | 604/329 |
| 2-21812 | of 0000 | Japan . | |
| 3-27623 | of 0000 | Japan . | |
| 2-30320 | of 0000 | Japan . | |
| 2-31754 | of 0000 | Japan . | |

Primary Examiner—Randall L. Green
Assistant Examiner—Elizabeth M. Burke
Attorney, Agent, or Firm—Haverstock, Garrett & Roberts

[57] ABSTRACT

A urinary collector for women comprising a urinary collector body formed of soft, flexible water-proof material, the collector body including a first or upper portion forming a water-permeable skin contacting face having a cup-like member associated therewith for fitting snugly to the vulva and receiving a urinary flow. The cup-like member is formed of a flexible water permeable material so as to allow urine to pass therethrough. The collector body also includes a second opposite or lower portion forming a urinary flow chamber, the urinary flow chamber being separated from the skin contacting face by a water impermeable membrane. A moisture absorbent material is located between the water impermeable membrane and the skin contacting face. The urinary flow chamber is packed with a hydrophobic material having a plurality of passages therethrough and is also provided with a urinary discharge outlet, the packed hydrophobic material maintaining the shape of the device when fitted for use. Urine discharged into the cup-like member passes therethrough into the urinary flow chamber. Once in the urinary flow chamber, the flow of urine through the urinary flow chamber is buffered by passage through the hydrophobic material and is thereafter discharged from the urinary flow chamber through the urinary discharge outlet.

8 Claims, 2 Drawing Sheets

URINARY COLLECTOR FOR WOMEN

Applicant hereby claims foreign priority benefits under 35 USC §119 of corresponding Japanese patent application Serial No. (Hei) 3-313472, filed Nov. 1, 1991.

BACKGROUND OF THE INVENTION

1. Field Of The Invention

The present invention relates to a urinary collector for women and, more particularly, to a collector device which can be worn discretely under clothing and undergarments to receive urinary discharges and comfortably, yet snugly fits directly around a user's vulva and urethral meatus, such that the rest of the surrounding pelvic area is not exposed to urine. The present urinary collector device buffers the flow of urine from the urethra without the urine backflowing and accumulating around the vulva such that the vulva can remain relatively dry and sanitary, and the device smoothly and evenly discharges the urine directly to other urine receiving and holding means such as a urinal bag or the like. The present collector is particularly adaptable for use on women who, for instance, have a urinary incontinence condition such as due to injury, disease and the like, women who are bedridden or are not sufficiently mobile or ambulatory to walk to a restroom or latrine such as due to advanced age, or physical handicaps, and women who suffer from dysuria (dysuriacs), which is a difficulty or pain in discharging urine.

2. Description of the Prior Art

Known urinary collector devices for women include catheter type devices including a tube which is inserted into and fixed in position in the urethra; diaper type garments wherein an absorbent material is fitted around the vulva region for receiving and absorbing urine therein; polyethylene bag type appliances wherein the polyethylene bag is adhered to the vulva using pressure sensitive adhesives and the excreted or discharged urine is introduced therein and received thereby; and molded type appliances wherein a rubber or plastic member is molded in a boat or cup shape, attached securely to the vulva by means of a supporter and also connected to a urinal collector bag or other receiving means, such as disclosed in Japanese Unexamined Patent Application Publication No. Hei 2-31754, Japanese Examined Patent Application Publication No. Hei 2-21812, and Japanese Examined Utility Model Application Publication No. Hei 3-27623.

Such prior art devices, however each have important limitations and shortcomings. For instance, risk of fungal infection, such as urethral infection, nephritis cystitis and the like, prevents long-term application of catheter devices unless under direct physician control. The diaper and diaper-type devices expose a wide area of the pelvic area to urine for a long time after urination which causes discomfort and makes the wearer susceptible to dermatitis and infection. Also, the attachment and removal of the diaper requires substantial effort for bedridden patients. The polyethylene bag type of collector reduces fecal contamination related infections since the vulva can be fitted independent of the anus, however, the device has troublesome problems associated with the shaving of pubic hair, dermatitis caused by adhesives, and urine leakage which cannot be completely prevented because of the complicated structure of the vulva. Use of a molded plastic collector appliance secured with a supporter includes a risk of urine leakage because the whole appliance cannot be uniformly fixed to the body when the user moves or reclines and also raises a risk of harm to the vulva from the hard plastic appliance.

Japanese Unexamined Utility Model Application No. Hei 2-30320 discloses a urinary collector comprising a skin contacting portion and a urine receiving bag-shaped portion, the skin contacting portion including a skin barrier portion which covers the pelvic region from approximately the mons pubis region to the perineum region, and having an opening positioned so as to correspond to the location of the urethral meatus. The urinary receiving portion of the collector is made of soft material and is connected to the skin contacting portion so that the urinary receiving portion surrounds the opening under the skin contacting side. This prior art collector as a whole is compact and flexible, and urine seldom leaks due to its close proximity to the wearer's skin. But this prior art device still enables urine to remain in direct contact with the wearer's skin because the material comprising the collector's skin barrier retains the urine and does not effectively transport the urine away from the wearer. In addition, excreted urine is not transmitted promptly from the collector to the urinal bag through the discharge outlet and can backflow toward the urethral meatus, which may cause dermatitis and fungal infections. Still further, increasing the adhesiveness of the skin barrier portion to avoid these problems is counter-beneficial due to the discomfort associated with removal of such adhesive in contact with the pubic hair.

SUMMARY OF THE INVENTION

The present urinary collector device for women overcomes many of the above-discussed disadvantages and shortcomings associated with the known prior art devices and teaches the construction and operation of an improved urinary collector device for women which can be comfortably and discretely worn and which effectively receives and buffers the flow of discharged urine without backflow and directs the urine into a urinal bag or other collecting means.

The present urinary collector for women provides a urinary collector body portion which is made of waterproof, soft material formed in a boat or a boat-like shape. The upper portion of the urinary collector body includes a water permeable, skin contacting face capable of covering the pelvic region from about the mons pubis to about the perineum. The urinary collector body also includes a cup-like opening located in the front-center portion of the face, so as to surround the urethral meatus and seal against the vulva with means for forming a water impermeable leak resistant fit. The urinary collector body further includes a urinary flow chamber located in the lower part of the collector body away from contact with the wearer, separated from the skin contacting portion by a water resistant membrane and separated from the opening in the contacting portion by a water permeable membrane which restrains a plurality of hydrophobic medium of material such as a plurality of hydrophobic beads. Hydrophobic beads can comprise granules or small flakes which can have various shapes such as spherical shapes, cylindrical, barrel, circular or other suitable shapes. The urinary flow chamber also includes an outlet opening adjacent to the lowermost portion thereof through which the urine can be discharged from the device into collecting means.

The urinary flow chamber also includes water absorbent material packed in a space between the contacting face portion and the water resistant membrane separating the skin contacting face and the urinary flow chamber.

The boat-like shaped urinary collector body is constructed of a flexible material. Location of the plurality of hydrophobic beads adjacent to the lower end portion of the urinary collector body acts to maintain the shape of the urinary collector body and positions the hydrophobic beads for receiving and buffering the discharge flow of the urine. In operation, the present collector is fitted only by pushing the skin contacting face portion directly against the vulva without an intervening adhesive layer or the like. When urination occurs, discharged urine is communicated to the opening through the water permeable membrane which forms the walls of the opening and into the urinary flow chamber, wherein the urine can flow smoothly along the surface of the individual hydrophobic beads through interstices therebetween downwardly through the urinary flow chamber under the influence of gravity without flowing upwardly back into the opening or the contacting face portion. Urine is directed from the device through the discharge outlet and into separate urine holding means as can be attached thereto, for instance, a tube communicating with a urinal bag, which separate holding means do not form part of the Present invention. The urine leaked aside from the urethral meatus and not entering the opening, will be absorbed through the skin contacting face portion into the absorbent material contained in the urinary flow chamber.

It is therefore an object of the present invention to provide a urinary collector for women which is capable of covering a region from almost the mons pubis to about the perineum which urinary collector receives and buffers the flow of discharged urine and drains the urine to urine collecting or holding means.

Another object is to provide a urinary collector for women which buffers the flow of discharged urine without the urine flowing back towards the vulva and collecting therearound.

Another object is to provide a urinary collector for women which can maintain the vulva area in a relatively dry and sanitary condition.

Another object is to provide a urinary collector for women which is quickly and easily attachable and detachable to the body and to the undergarments without assistance.

Another object is to provide a urinary collector for women which is comfortable to wear and use.

Another object is to provide a urinary collector for women which can be discretely worn.

Another object is to provide a urinary collector that is not easily compressible or crushable.

Another object is to provide a urinary collector for women which does not increase the difficulty of or pain from urination for persons suffering from dysuria.

Another object is to provide a urinary collector for dysuriac women which does not increase physical or psychological resistance to urination.

These and other objects and advantages of the present urinary collector for women will become apparent after considering the following specification in conjunction with the accompanying drawings wherein:

DESCRIPTION OF THE PREFERRED EMBODIMENT

Figure 1:
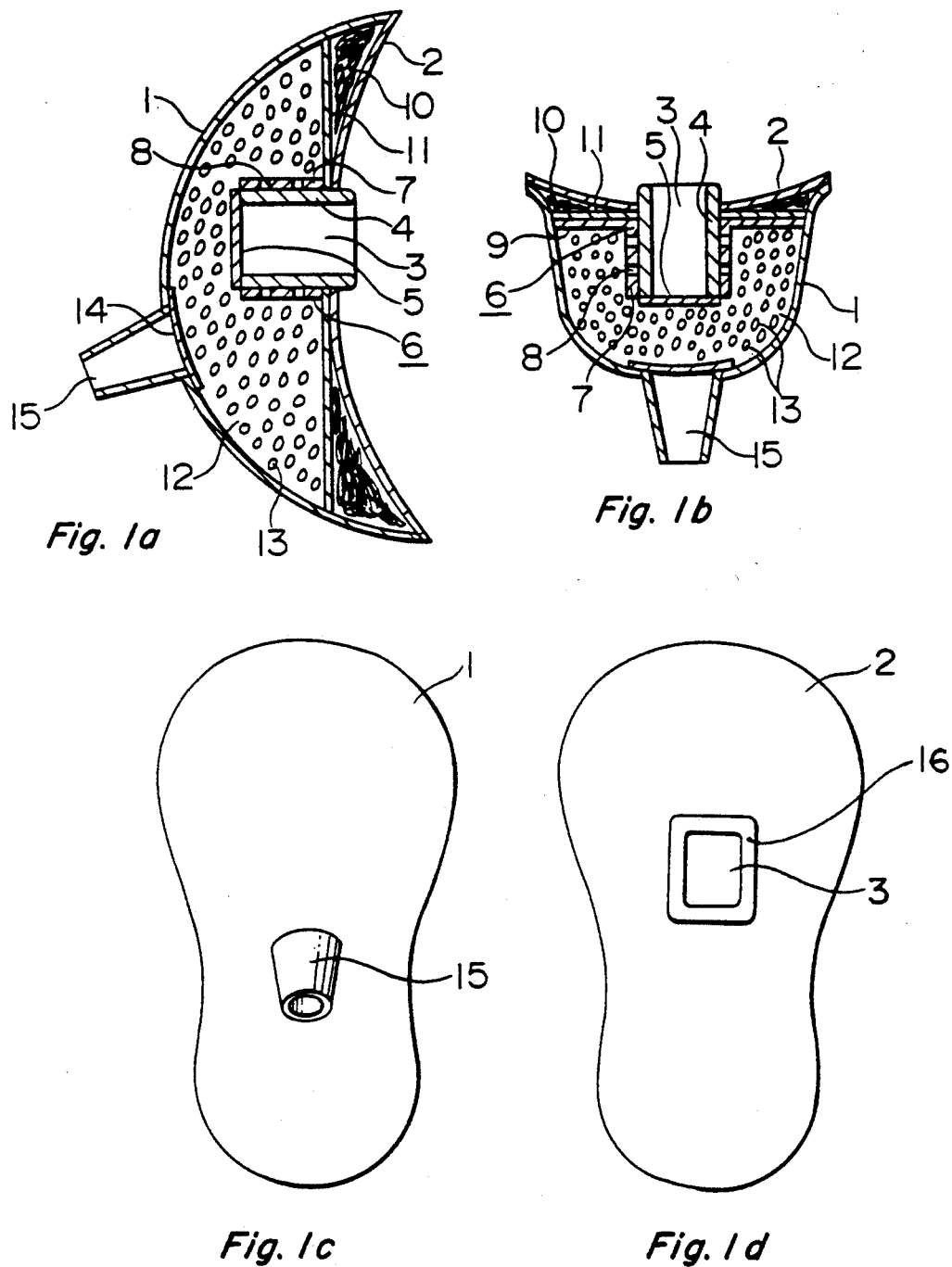
FIGS. 1a and 1b are cross sectional views, respectively.
FIGS. 1c and 1d are a bottom view and a top view, respectively, of a urinary collector for women constructed according to the teachings of the present invention.

The present invention will be described in detail with reference to the attached drawings.

Referring to the drawings more particularly by reference numbers wherein like numerals refer to like parts, FIGS. 1a, 1b, 1c and 1d show one embodiment of a urinary collector device for women wherein the numeral 1 identifies a urinary collector body made of a waterproof, soft and thin material formed into a boat or boat-like shape. The urinary collector body 1 has opposite sides extending between opposite ends thereof and includes a skin contacting face 2, which skin contacting face 2 is sized and shaped for locating in contact with a woman's vulva. The skin contacting face 2 is constructed of a thin, flexible film having numerous pores therethrough sufficient for the passage of leaked urine away from the skin surface. An opening 3 extends through the skin contacting face 2 adjacent approximately the front center or central portion thereof. The opening 3 is formed by a small chamber having a cup shape, which chamber is constructed of a highly elastic material, the side face of which is formed of a water permeable foam material 4, the bottom face of which is formed by a water permeable membrane 5. The opening 3 is preferably of a rectangular shape defined by the water permeable foam side face 4, which rectangular shape is maintained by a supporting frame 6. The supporting frame 6 is preferably a T-shaped member, the leg portion 7 of which is formed into a rectangular shaped channel or tube which extends around the side face 4. The inside surface of the leg portion 7 is located adjacent the outside of the surface foam material 4 defining the opening 3 and is attached thereto. The leg portion 7 includes a plurality of holes 8 extending therethrough to enable the rapid passage of urine out of the opening 3. The cross portion of the supporting frame 6 forms a flange portion 9 which extends around the opening 3 and radially outwardly therefrom toward the opposite sides of the urinary collector body 1, the opposed radially outermost portions of the flange 9 being attached to the inner surface of the urinary collector body 1.

The urinary collector body 1 includes an enclosed space which contains a water absorbent material 10 located adjacent the inside surface of the porous skin contacting face 2. The water absorbent material 10 is packed against the inside of the skin contacting face 2 and is maintained in such position by a water resistant membrane 11. The internal cavity of the urinary collector body 1 forms a urinary flow chamber 12 which is packed with a hydrophobic medium, preferably a plurality of beads 13 formed of a water repelling hydrophobic material relatively tightly packed in the chamber 12.

The urinary flow chamber 12 also includes a discharge outlet 15 located opposite the waterproof membrane 11 adjacent the lowermost portion of the urinary flow chamber. The discharge outlet 15 is covered by a water permeable membrane 14 so as to enable the passage of urine therethrough but yet contain the hydrophobic beads 13 therewithin.

The urinary collector body 1 and the supporting frame 6 can be constructed of any suitable material such as plastic foam sheet material, flexible plastic sheet, and the like. The plastic foam sheet material can comprise polyethylene or ethylene-vinyl acetate copolymer, which are the preferred materials, and can further include polypropylene polyvinyl chloride, polystyrene, polybutadiene and polyurethane. The plastic foam sheet material should have an expansion ration from about 5 to 1 to about 50 to 1, and can have the thickness from about 0.5 mm to about 5 mm, and is preferably from about 1 mm to about 2 mm thick. The alternative flexible plastic sheet material can comprise any suitable plastic sheet material such as polyethylene, ethylene-vinyl acetate copolymer, polyamide/polyethylene composite sheet, polypropylene, polyvinyl chloride and various other composite plastic sheet materials. The flexible plastic sheet can have a typical thickness from about 0.03 mm to about 1 mm.

The skin contacting face 2 material can comprise a film having pores extending therethrough which allow water transmission, or alternatively, a film or net fabric, and can be fabricated from flexible polyethylene, ethylene vinyl acetate copolymer, urethane, polyvinyl chloride and polyvinyl alcohol. The skin contacting face can have a film thickness from about 10 micrometers to about 200 micrometers. Of the above materials for the skin contacting face 2, a film of net fabric made from flexible polyethylene is preferred. Alternatively, nonwoven fabric of polyethylene, polypropylene, polyester, acrylic, and rayon or a combination of these materials may also be used.

The water permeable membranes 5 and 14 can comprise a woven or nonwoven fabric, porous plastic sheet, or plastic net material. The woven and nonwoven fabric can be constructed of polyester, polyethylene, polypropylene, rayon and polyurethane, while the porous plastic sheet and plastic net can be constructed of polyethylene, ethylene-vinyl acetate copolymer, and polypropylene. The pore size of the water permeable membrane can be from about 0.05 mm to about 3 mm.

The hydrophobic beads 13 can be fabricated from polyethylene, polystyrene, and polypropylene, and the like, and alternatively, ceramics such as glass. The preferred foam material being of polyethylene, polystyrene or polypropylene. The hydrophobic beads 13 can have various shapes and sizes including a spherical shape having diameters from about 0.5 mm to about 5 mm, a columnar shape having a diameter and a height dimension of from about 1 mm by 50 mm to about 5 mm by 50 mm, a circular shape having a diameter from about 5 mm to about 20 mm, crepe material having a thickness from about 1 mm to about 5 mm and a length from about 10 mm to about 30 mm, and a cylindrical shape having an outer diameter from about 3 mm to about 20 mm and a height from about 5 mm to about 20 mm, may be used. The number of hydrophobic beads can be determined for a particular application depending on the anticipated urination quantity, with the number of beads corresponding to a volume of about 30 cc to about 200 cc, and a typical volume of about 130 cc. The hydrophobic beads 13 can further be treated or mixed with a bacteriacide or deodorant, as desired.

The water absorbent material 10 can comprise nonwoven fabric made of cotton, staple fiber, polyester, acrylic, polyethylene, or polypropylene, and the like having a weight per unit area from about 20 g/m$^2$ to about 300 g/m$^2$ can be used. Alternatively, a combination of the above-referenced nonwoven fabric and a high polymeric absorbent ca also be used.

The side 4 of the cup shaped member forming the opening 3 can be formed of a water permeable elastic foam material such as polyurethane, polyvinyl chloride, natural rubber, synthetic rubber, and the like. The cup shaped member may be molded so as to form a rectangular shaped opening 3, as shown, and alternatively, a parallel piped, oval, barrel or other shape, having a width from about 15 mm to about 50 mm, and a length from about 30 mm to about 100 mm, and a depth from about 20 mm to about 50 mm. The edge 16 of side wall 4 directly in contact with the vulva area and extending above the surface of the skin contacting face preferably comprises a flexible water-impermeable foam material of closed cell construction.

The required volume and buffer capacity of the urinary flow chamber are approximately determined from the difference between the estimated discharge flow rate possible through the discharge outlet 15 compared to the estimated urinary flow rate. A urinary flow chamber volume can range from about 30 cc to about 200 cc, with a volume of about 130 cc being typical.

OPERATION

Figure 2:
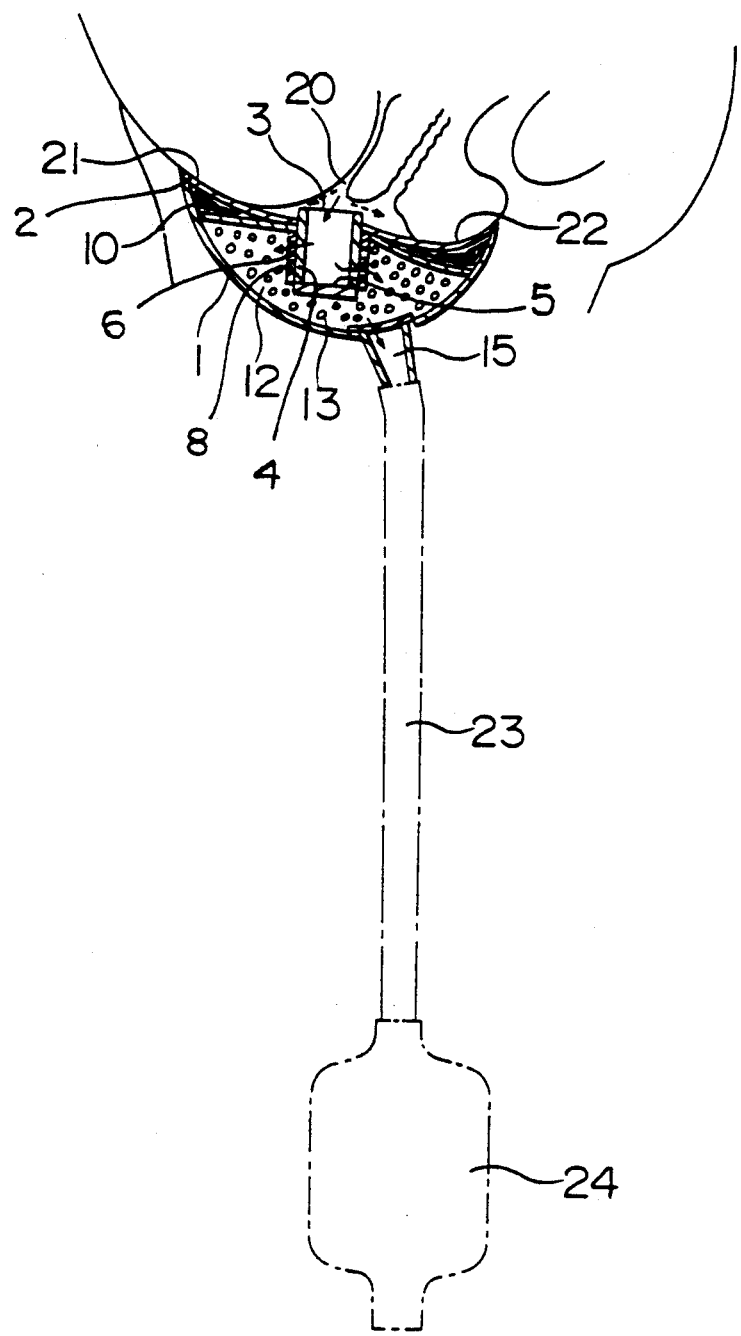
FIG. 2 is a cross sectional view of the urinary collector for women of FIG. 1 shown attached to the female genitalia in position for use, and showing in association therewith in phantom lines a urinal bag and a connector tube, which urinal bag and connector tube do not form part of the present invention.

The manner of usage and operation of a urinary collector for women constructed according to the teachings of the present invention will be explained referring to FIG. 2. The urinary collector body 1 is fitted to the vulva so as to extend from approximately the mons pubis 21 to approximately the perineum area 22, such that the opening 3 is positioned in opposing and covering relation to the urethral meatus 20. The wearer can then place undergarments (not shown) over the pelvic region with the urinary collector body 1 fitted snugly to the genitalia. The outside of the urinary collector body 1 can then be fixed or adhered to the inside of the undergarment by means such as pressure sensitive double coated adhesive tape (not shown). Urine collection means, for instance a tube 23 connected to a urinal bag 24, can be attached to the discharge outlet 15 of the collector body 1, as shown.

When urination occurs, the urine discharged from the urethral meatus 20 enters into the opening 3 as indicated by an arrow, while a portion of the urine as indicated by the broken arrow passes through the water permeable skin contacting face 2 and is absorbed by the water absorbent material 10 adjacent thereto. Urine entering the opening 3 passes through the water permeable foam material side 4 and through holes 8 in the supporting frame 6, and also through the water permeable membrane 5 into the urinary flow chamber 12. In the urinary flow chamber 12, the urine flows downwardly along the surfaces of the hydrophobic beads 13 and between the interstices therebetween. The packed plurality of hydrophobic beads 13 acts to maintain the required volume of the urinary flow chamber 12 such that the flow of urine is buffered in the urinary flow chamber 12 with the urine temporarily building up in the chamber 12. Importantly, the hydrophobic characteristic of the beads 13 prevents absorption of the urine thereby and enables the urine to flow smoothly around the beads 13. Urine which reaches the discharge outlet 15 is then transmitted through the tube 23 to the urinal bag 24.

A urinary collector for women constructed according to the teachings of the present invention, including a urinary collector body 1 fabricated from a soft material and including a urinary flow chamber packed with hydrophobic beads, provides a relatively light, small urinary collector device which can be placed compactly and discretely inside a user's undergarment without compression or crushing of the device. This reduces the wearer's discomfort and enables easy attachment by fitting the urinary collector around the genitalia and adhering it to the wearer's undergarment without requiring typical supporter means such as belts and the like which require more labor for attachment thereof. Also importantly, the present device lessens the occurrence of possible pain when worn caused by the device pulling pubic hair. Detachment of the present device is also made easier by the simple attachment means. Another important advantage of the present urinary collector is that backflow of urine is prevented by the use of a relatively simple structure in the form of the urinary flow chamber containing hydrophobic beads located at an intermediate position in the urinary discharge path. Still further, the structure of the present urinary collector is very simple, inexpensive to produce and enables hygenic and sanitary usage and disposable. Also importantly, the present invention is similar in appearance and texture to sanitary napkins so as to be more readily acceptable by dysuriac women.

Thus there has been shown and described a novel urinary collector for women, which construction fulfills all of the objects and advantages sought therefor. Many changes, modifications, variations, and other uses and applications of the present construction will, however, become apparent to those skilled in the art after considering this specification and the accompanying drawings. All such changes, modifications, variations, and other uses and applications which do not depart from the spirit and scope of the invention are deemed to be covered by the invention which is limited only by the claims which follow.

What is claimed is:

1. A urinary collector for women to receive urinary discharge comprising a urinary collector body member having wall means and a top portion defining a chamber therebetween for collection and transfer of urinary discharge, said wall means being constructed of a waterproof, soft material, said top portion being constructed of a thin water permeable film having an outer surface forming a skin contacting face, said chamber being partitioned by a water impermeable film into a first chamber portion located between said impermeable film and said top portion and a second chamber portion located therebelow, said first chamber portion being packed with a water absorbing material, said second chamber portion being packed with hydrophobic material having interstices forming passages therethrough, a cup member extending through said top portion and through said impermeable film into said second chamber portion, said cup member being position and located for receiving urinary discharge and being constructed of a water permeable material, said urinary collector body member having an outlet opening communicating with said second chamber portion, and means for preventing passage of the hydrophobic material through said outlet opening.

2. The urinary collector for women according to claim 1 wherein said cup member further comprises a rim portion extending outwardly above the skin contacting face of said top body portion, said rim portion being constructed of a flexible, water impermeable material.

3. A urinary collector for women positionable in abutting relation to a women's pelvic region extending from approximately her mons pubic region to approximately her perineum region and including her urethra, said urinary collector comprising a urinary collector body member having wall means and a top portion defining a cavity therewithin, said wall means being constructed of waterproof, soft material, said top portion being constructed of a thin water permeable film having an outer surface forming a skin contacting face sized and shaped for positioning in abutting relation to the women's pelvic region, said cavity being partitioned into two portions by a water impermeable film having opposed sides including a first cavity portion located adjacent one side of said water impermeable film and a second cavity portion located below and adjacent an opposite side thereof, said first cavity portion being packed with a water absorbing material and said second cavity portion forming a urinary flow chamber, said urinary flow chamber being packed with a hydrophobic material having interstices extending therethrough, a cup-shaped member extending through said top portion and through said impermeable film into said urinary flow chamber, said cup-shaped member being fabricated from a water permeable material and being positioned and located at approximately a central location on said skin contacting face so as to be approximately opposite the urethra when placed in operative position, said urinary collector body member having an outlet opening communicating with said urinary flow chamber, and means for preventing passage of the hydrophobic material through said outlet opening.

4. The urinary collector for women according to claim 3 wherein said cup-shaped member has a rectangular opening.

5. The urinary collector for women according to claim 3 further comprising means adjacent the outlet opening for attaching urine receiving and collecting means thereto.

6. The urinary collector for women according to claim 3 wherein said hydrophobic material includes a plurality of hydrophobic beads.

7. The urinary collector for women according to claim 6 wherein said hydrophobic beads are constructed of a material selected from the group consisting of polyethylene foam, polystyrene foam and polypropylene foam.

8. The urinary collector for women according to claim 6 wherein said hydrophobic beads are made from a ceramic material.

* * * * *

UNITED STATES PATENT AND TRADEMARK OFFICE
CERTIFICATE OF CORRECTION

PATENT NO. : 5,295,983
DATED : March 22, 1994
INVENTOR(S) : Yoshinori Kubo

It is certified that error appears in the above-indentified patent and that said Letters Patent is hereby corrected as shown below:

Column 6, line 9, "cs" should be --can --.

Signed and Sealed this

Twenty-sixth Day of July, 1994

Attest:

BRUCE LEHMAN

Attesting Officer

Commissioner of Patents and Trademarks